United States Patent [19]

King et al.

[11] 4,237,121
[45] Dec. 2, 1980

[54] SUBSTITUTED OXADIAZOLES AND THEIR USE AS CORN ROOT WORM INSECTICIDES

[75] Inventors: William F. King, Novato; Ronald E. Wheeler, Martinez, both of Calif.

[73] Assignee: Chevron Research Company, San Francisco, Calif.

[21] Appl. No.: 48,560

[22] Filed: Jun. 14, 1979

Related U.S. Application Data

[63] Continuation of Ser. No. 943,078, Sep. 18, 1978, abandoned.

[51] Int. Cl.³ .................... A01N 57/00; A01N 57/26
[52] U.S. Cl. .................................................. 424/200
[58] Field of Search ........................................ 424/200

[56] References Cited

U.S. PATENT DOCUMENTS 3,920,677  11/1975  Meyer et al. .................... 424/272
4,028,377   6/1977  Meyer et al. .................... 424/200

*Primary Examiner*—Douglas W. Robinson
*Attorney, Agent, or Firm*—D. A. Newell; T. G. DeJonghe

[57] ABSTRACT

A method for killing corn root worms by applying to the soil habitat of the root worms an insecticidal amount of the compound of the formula

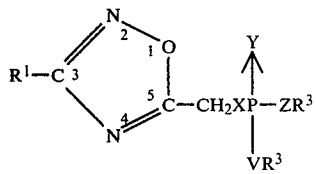

wherein $R^1$, $R^2$ and $R^3$ are alkyl of 1 to 4 carbon atoms; and X, Y, Z and V are sulfur or oxygen.

4 Claims, No Drawings

SUBSTITUTED OXADIAZOLES AND THEIR USE AS CORN ROOT WORM INSECTICIDES

This is a continuation of application Ser. No. 943,078, filed Sept. 18, 1978 now abandoned.

RELATED APPLICATION

The present application is related to our concurrently filed application entitled "Use of Oxadiazole Derivatives for Corn Root Worm Control", the disclosure of which application is incorporated herein by reference.

BACKGROUND OF THE INVENTION

The present invention relates to the use of certain oxadiazole derivatives use as corn root worm insecticides.

British Pat. No. 1,213,707 discloses insecticidal compounds of the general formula $$\underset{R_2}{\overset{R_1O}{>}}\overset{X_1}{\underset{\|}{P}}-X_2-A-\underset{\underset{O}{\diagdown}\diagup}{\overset{N}{\diagup\diagdown}}-R_3$$

wherein $X_1$ and $X_2$, which may be the same or different, each represents an oxygen or sulfur atom; A represents an alkylene group; $R_1$ represents an alkyl group, $R_2$ represents an alkyl or alkoxy group; and $R_3$ represents a hydrogen atom or an optionally substituted carbamoyl or amino group. A particular species disclosed in the British patent at Table 2, 9th compound from the top, is 3-(diethoxyphosphinothioylthiomethyl)-5-methyl-1,2,4-oxadiazole.

The examples of the British patent show testing of certain of the compounds for insecticidal activity on adult houseflies: mosquito larvae, diamond back moth larvae, aphids and adult mustard beetles; red spider mites; and white butterfly larvae. None of these tests involved application and use of the insecticide in the soil habitat of the insects.

U.S. Pat. No. 4,028,377 discloses insecticidal compounds of the general formula $$R_1-\underset{N}{\overset{O\text{------}N}{\diagup\diagdown}}-CH_3-S-\overset{O}{\underset{\|}{P}}\overset{OR_3}{\diagdown SR_2}$$

wherein $R_1$ represents hydrogen, unsubstituted alkyl, benzyl or phenyl, $R_2$ represents methyl or ethyl, and $R_3$ represents unsubstituted $C_1$-$C_7$ alkyl optionally interrupted by oxygen or represents $C_3$-$C_4$ alkenyl.

The examples of the 4,028,377 patent show testing of certain of the compounds for insecticidal activity on ticks in cotton wool; larvae of ticks; mites; and on root-gall-nematodes in soil. In the latter test, the soil infested with the root-gall-nematocides was treated with the compounds to be tested and then tomato seedlings were planted either immediately after the soil preparation or after 8 days waiting.

British Pat. No. 1,261,158 discloses compounds of the general formula $$\underset{R_2}{\overset{R_1O}{>}}\overset{X}{\underset{\|}{P}}-S-A-\underset{\underset{O}{\diagdown}\diagup}{\overset{N}{\diagup\diagdown}}-(Y)_n$$

The first compound disclosed in Table I of British Pat. No. 1,261,158 is 5-(diethoxyphosphinothioylthiomethyl)-3-methylisoxazole. The compounds of the examples of British Pat. No. 1,261,158 was tested for insecticidal effectiveness on flies, mosquito larvae, moth larvae, mustard beetles, aphids, spider mites and butterfly larvae.

As described in the Ortho Seed Treater Manual, copyright 1976, Chevron Chemical Company, page 27, corn root worms have been controlled with chlorinated hydrocarbon insecticides, but in areas where resistance to such treatment has developed, good control has been obtained with organic phosphorus or carbamate soil insecticides such as Diazinon and Carbofuran insecticides. The chemical names and formulas for these latter insecticides is given below:

Diazinon insecticide: O,O-diethyl O-(2-isopropyl-4-methyl-6-pyrimidinyl)phosphorothioate Carbofuran insecticide: 3,3-dihydro-2,2-dimethyl-7-benzo-furanyl-methylcarbamate

SUMMARY OF THE INVENTION

According to the present invention a method is provided for killing corn root worms which comprises applying to the soil habitat of the root worms an insecticidally effective amount of a compound of the formula $$R^1-\underset{N}{\overset{N}{\underset{\diagdown}{\overset{2}{C}}\underset{\diagup}{\overset{1}{O}}}}\underset{4}{\overset{}{\underset{5}{C}}}-CH_2XP\overset{Y}{\underset{\underset{VR^3}{|}}{-}}ZR^3 \quad (I)$$

wherein $R^1$, $R^2$ and $R^3$ are alkyl of 1 to 4 carbon atoms; and X, Y, Z and V are sulfur or oxygen.

Among other factors, the present invention is based on our unexpected finding that compounds in accordance with the present invention have especially high activity against corn root worms when the compound is applied in the soil habitat of the corn root worm.

Preferred compounds for use in this embodiment include those wherein $R^2$ and $R^3$ are ethyl and, more preferably, wherein the compound is further defined in that Y is sulfur and Z and V are oxygen. Most preferably, the compound used is one wherein the compound is still further defined in that $R^1$ is methyl and X is sulfur.

According to another alternative embodiment of the present invention there is provided a corn root worm insecticidal composition comprising a corn root worm-insecticidally effective amount of a compound of the formula I, wherein $R^1$, $R^2$ and $R^3$ are alkyl of 1 to 4 carbon atoms; and X, Y, Z and V are sulfur or oxygen; and a biologically inert carrier. Preferably the compound used in this embodiment of the present invention is 3-methyl-5-(diethoxyphosphorothioylthiomethyl)-1,2,4-oxadiazole.

The term "corn root worm" is used herein to include the Northern, Southern and Western species of the corn root worm. All of these are of the Diabrotica genus. The scientific name of the Northern species is *Diabrotica longicornis*, the scientific name of the Southern species is *Diabrotica duodecimpunctata*, and the scientific name of the Western species is *Diabrotica virgivera*.

The compounds used in the present invention may be prepared by subjecting 3-alkyl-5-chloromethyl-1,2,4-oxadiazoles (II) to a phosphorylation reaction.

The 3-alkyl-5-chloromethyl-1,2,4-oxadiazoles (II) were prepared by condensing the appropriate alkylamidoximes (obtained from nitriles—see Chem. Revs. 61 155 (1961) with chloroacetyl chloride.

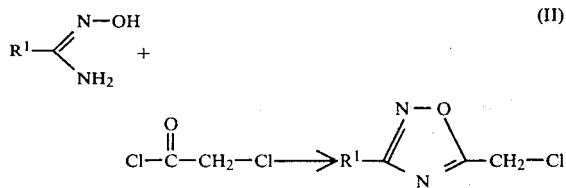

The 5-chloromethyl-1,2,4-oxadiazoles were phosphorylated with phosphate salts of the general formula (III) to give (I) above:

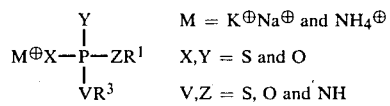

M = K⊕ Na⊕ and NH4⊕
X,Y = S and O
V,Z = S, O and NH

This last reaction can be carried out in a number of solvents, e.g., acetone, acetonitrile, ether, methanol, benzene, etc. Preferably equimolar amounts of reactants are employed, although a small excess of either may be employed. Either reactant may be added to the other reactant in the solvent; however, it is preferred to add the solid phosphate salt to a solution of the chloromethyloxadiazole. The addition is carried out at temperatures in the range of 15°–30° C. Upon completion of addition of the salt, the temperature of the reaction is raised, preferably to the reflux temperature.

The reaction is generally complete in 1–5 hours. At completion of the reaction, the product reaction mixture is filtered to remove any insoluble salts. The filtrate is then stripped of solvent under reduced pressure to give crude 3-alkyl-5-(dialkoxyphosphorothioylthiomethyl)-1,2,4-oxadiazole. The crude material can be purified by column chromatography (silica gel) and eluting with hydrocarbons and chlorinated hydrocarbons.

EXAMPLES

EXAMPLE 1—PREPARATION METHODS (a) Acetamidoxime

Acetonitrile was added to a previously stirred solution of 0.55 mol hydroxylamine hydrochloride and 0.55 mol anhydrous sodium carbonate in 750 ml of absolute ethanol. This mixture was stirred for 0.5 hour at room temperature and then refluxed at 55°–70° C. for 24 hours. The reaction was cooled and filtered, the solid residue slurried in warm acetone and refiltered, the filtrates were combined and concentrated to an oil under reduced pressure. The oil was again taken up in acetone-ether to rid the system of dissolved inorganic salts. The acetone-ether filtrate was concentrated under reduced pressure, the oil was then triturated with ether-hexane leaving a white solid. Infrared (IR) and nuclear magnetic resonance (NMR) elemental analysis indicated the acetamidoxime (m.p. 128°–133°).

(b) 3-Methyl-5-Chloromethyl-1,2,4-Oxadiazole

Acetamidoxime (14.1 g) was placed in 200 ml of benzene in a 3-necked, round-bottom flask equipped with a mechanical stirrer, condenser and dropping funnel charged with 23 g of chloroacetyl chloride. The benzene slurry was increased in temperature to near reflux, and the chloroacetyl chloride was added dropwise to the refluxing mixture. A Dean-Stark trap was added and refluxing continued for 3 hours. The reaction mixture was cooled and 100 ml benzene added, washed (3 × 125 ml) with water, dried with anhydrous MgSO4, and solvent removed under reduced pressure, leaving the desired product as an amber liquid (confirmed by IR, NMR and elemental analysis).

(c) 3-Methyl-5-(diethoxyphosphorothioylthiomethyl)-1,2,4-oxadiazole 3-methyl-5-chloromethyl-1,2,4-oxadiazole (0.04 mol) was dissolved in acetone and ammonium O,O-diethyldithiophosphate (0.04 mol) was added with stirring in several portions. The reaction was then refluxed for 3 hours, cooled and filtered. The solvent was removed under reduced pressure leaving an amber oil which was chromatographed (silica gel) and eluted with hexane:-methylene chloride (80%). The phosphate was obtained as an almost colorless oil.

EXAMPLES 2–32—COMPOUND TESTING

The substituted oxadiazole compounds were tested for control of corn root worm (Diabrotica larvae), by the following procedure:

A batch of 20 to 30 two-day-old Diabrotica eggs is placed on the bottom of a 237-cc clear plastic cup. These eggs are then covered with about 45 cc's of soil containing 15 ppm of the test compound. The soil is watered with 15 cc of water. The corn seeds, presoaked for 2 hours, are evenly distributed on the soil surface. Then an additional 45 cc's of the same treated soil is added to cover the seeds, and this soil is watered with an additional 15 cc's of water. The test cup is kept at 70° C. with occasional light watering just to keep the soil damp.

After 14 to 16 days, the test unit is examined under a dissecting scope, by observing the corn roots and larvae through the cup's clear plastic walls. Control of newly hatched larvae is rated by visually evaluating the degree of corn root damage by feeding larvae in conjunction with the visible presence of live and/or dead larvae.

The compounds tested and the percent control of Diabrotica larvae are given in Table I. Unless otherwise indicated, the tests were done using 15 ppm of the test compound, on the basis indicated above.

TABLE I

| Ex. No. | Compound | Control, % |
|---|---|---|
| 2 | 3-isopropyl-5-(methoxy-N-ethylaminophosphinyl-thiomethyl)-1,2,4-oxadiazole | 0 |
| 3 | 3-(2'-pyridinyl)-5-(methoxy-N-ethylaminophosphinyl-thiomethyl)-1,2,4-oxadiazole | 0 |
| 4 | 3-isopropyl-5-(diethoxyphosphinothioylthiomethyl)-1,2,4-oxadiazole | 100;98* |
| 5 | 3-(1'-cyclohexenyl)-5-(diethoxyphosphinothioyl-thiomethyl)-1,2,4-oxadiazole | 0 |
| 6 | 3-(3',4'-dioxymethylenephenyl)-5-(diethoxyphos-phinothioylthiomethyl)-1,2,4-oxadiazole | 0 |
| 7 | 3-(2,4-dichlorobenzyl)-5-(aminomethoxyphosphinyl-thiomethyl)-1,2,4-oxadiazole | 0 |
| 8 | 3-isopropyl-5-(aminomethoxyphosphinylthiomethyl)-1,2,4-oxadiazole | 0 |
| 9 | 3-isopropyl-5-(dimethoxyphosphinothioylthiomethyl)-1,2,4-oxadiazole | 95 |
| 10 | 3-(3'-nitrophenyl)-5-(dimethoxyphosphinothioylthio-methyl)-1,2,4-oxadiazole | 0 |
| 11 | 3-isopropyl-5-(diethoxyphosphinothioylthioethyli-dene)-1,2,4-oxadiazole | 99.5*;100* 28*;22** |
| 12 | 3-(3'-nitrophenyl)-5-(diethoxyphosphinothioylthio-methyl)-1,2,4-oxadiazole | 1* |
| 13 | 3-(3'-nitrophenyl)-5-(aminomethoxyphosphinylthio-methyl)-1,2,4-oxadiazole | — |
| 14 | 3-methyl-5-(aminomethoxyphosphinylthiomethyl)-1,2,4-oxadiazole | 0* |
| 15 | 3-methyl-5-(diethoxyphosphinothioylthiomethyl)-1,2,4-oxadiazole | 100*;99** |
| 16 | 3-methyl-5-(dimethoxyphosphinothioylthiomethyl)-1,2,4-oxadiazole | 100*;99** 28* |
| 17 | 3-ethyl-5-(aminomethoxyphosphinylthiomethyl)-1,2,4-oxadiazole | 95*;95* |
| 18 | 3-ethyl-5-(dimethoxyphosphinothioylthiomethyl)-1,2,4-oxadiazole | 100*;98.5* |
| 19 | 3-ethyl-5-(diethoxyphosphinothioylthiomethyl)-1,2,4-oxadiazole | 100*;99.5* 98** |
| 20 | 3-(4'-nitrophenyl)-5-(dimethoxyphosphinothioyl-thiomethyl)-1,2,4-oxadiazole | 0 |
| 21 | 3-tertiarybutyl-5-(aminomethoxyphosphinylthio-methyl)-1,2,4-oxadiazole | 63 |
| 22 | 3-tertiarybutyl-5-(diethoxyphosphinothioylthio-methyl)-1,2,4-oxadiazole | 99*;99.5* 0**;98** |
| 23 | 3-tertiarybutyl-5-(dimethoxyphosphinothioylthio-methyl)-1,2,4-oxadiazole | 75*;95* 50 |
| 24 | 3-isopropyl-5-(methoxymethylthiophosphinylthio-ethylidene)-1,2,4-oxadiazole | 25 |
| 25 | 3-heptyl-5-(diethoxyphosphinothioylthiomethyl)-1,2,4-oxadiazole | 0 |
| 26 | 3-(diethoxyphosphinothioylthiomethyl)-5-(diethoxy-phosphinothioylthiomethyl)-1,2,4-oxadiazole | 0 |
| 27 | 3-(3'5'-dinitrophenyl)-5-(diethoxyphosphinothioyl-thiomethyl)-1,2,4-oxadiazole | 0 |
| 28 | 3-methyl-5-diethoxyphosphinothioyloxymethyl)-1,2,4-oxadiazole | 96*;100*; 100* |
| 29 | 3-tertiarybutyl-5-(dimethylaminomethoxyphosphinyl-thiomethyl)-1,2,4-oxadiazole | 0 |
| 30 | 3-heptyl-5-(methylaminomethoxyphosphinylthiomethyl)-1,2,4,-oxadiazole | 0 |
| 31 | 3-ethyl-5-(diethoxyphosphinothioylthioethyl)-1,2,4-oxadiazole | 0 |
| 32 | 3-(diethoxyphosphinothioylthiomethyl)-5-methyl-1,2,4-oxadiazole | 100;100* 100** |

*At 6.4 ppm of the test compound
**At 2.5 ppm of the test compound

We have found in our test work that certain relatively closely related compounds were not effective to control corn root worm. Those compounds showing little or no control in Table I above are excluded from the scope of the present invention. It may be noted that compounds within the scope of the present invention, in addition to being built from the oxadiazole ring, have a CH₂ linking group between the phosphorus-containing group and the oxadiazole ring, do not have N groups on the P atom, and have R¹ groups of no more than 1 to 4 carbon atoms.

The claims of the present invention do not include the use of Example 32 compound which, as indicated above under "Background of the Invention", has been disclosed, although for uses other than corn root worm control.

We claim:
1. A method for killing corn root worms which comprises applying to the soil habitat of the corn root worms an insecticidally effective amount of a compound of the formula

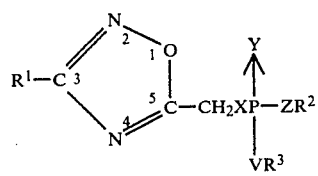

wherein $R^1$, $R^2$ and $R^3$ are alkyl of 1 to 4 carbon atoms; and X, Y, Z and V are sulfur or oxygen.

2. A method in accordance with claim 1 wherein $R^2$ and $R^3$ are ethyl.

3. A method in accordance with claim 2 wherein Y is sulfur and Z and V are oxygen.

4. A method in accordance with claim 3 wherein $R^1$ is methyl and X is sulfur.